United States Patent [19]

Fabish

[11] 4,121,580

[45] Oct. 24, 1978

[54] SQUEEZE BAG RESUSCITATOR WITH AIR-OXYGEN PROPORTIONING CONTROL

[75] Inventor: Donald Clayton Fabish, Anaheim, Calif.

[73] Assignee: Robertshaw Controls Company, Richmond, Va.

[21] Appl. No.: 766,184

[22] Filed: Feb. 7, 1977

[51] Int. Cl.² ............................................. A61M 16/00
[52] U.S. Cl. .............................. 128/145.7; 128/142.2; 128/210; 137/102; 137/491
[58] Field of Search ............... 128/145.7, 145.8, 145.6, 128/142.2, 209, 210, 205, 196, 197, 195; 272/99 R; 137/491, 102

[56] References Cited

U.S. PATENT DOCUMENTS

| 3,083,707 | 4/1963 | Seeler | 128/145.8 |
| 3,830,257 | 8/1974 | Metivier | 128/145.8 |
| 3,993,059 | 11/1976 | Sjostrand | 128/145.7 |
| 4,037,595 | 7/1977 | Elam | 128/145.7 |

*Primary Examiner*—Henry J. Recla
*Attorney, Agent, or Firm*—Fulwider, Patton, Rieber, Lee & Utecht

[57] ABSTRACT

There is disclosed a squeeze bag resuscitating device having an inhalation-exhalation valve with a gas supply to the squeeze bag that includes a proportionating valve which receives separate supplies of air and oxygen and which has a fixedly adjustable proportionating control member whereby the proportons of oxygen in the gas mixture can be fixedly adjusted to any of a plurality of preselected values. In a preferred embodiment, the proportionating valve is detachably mounted on the resuscitating device and can be interchanged with a demand valve such as that described in my prior U.S. Pat. No. 3,795,257.

17 Claims, 6 Drawing Figures

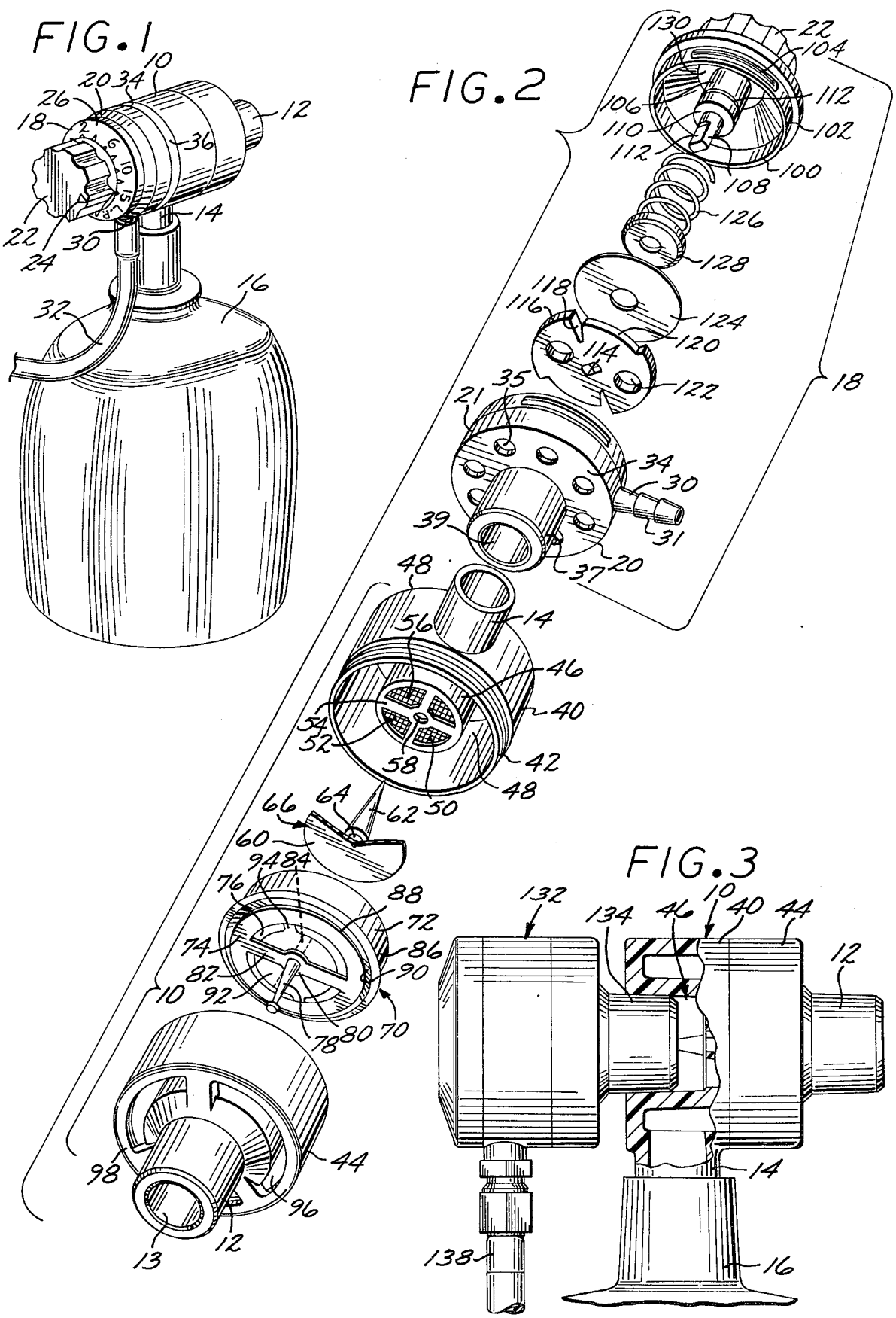

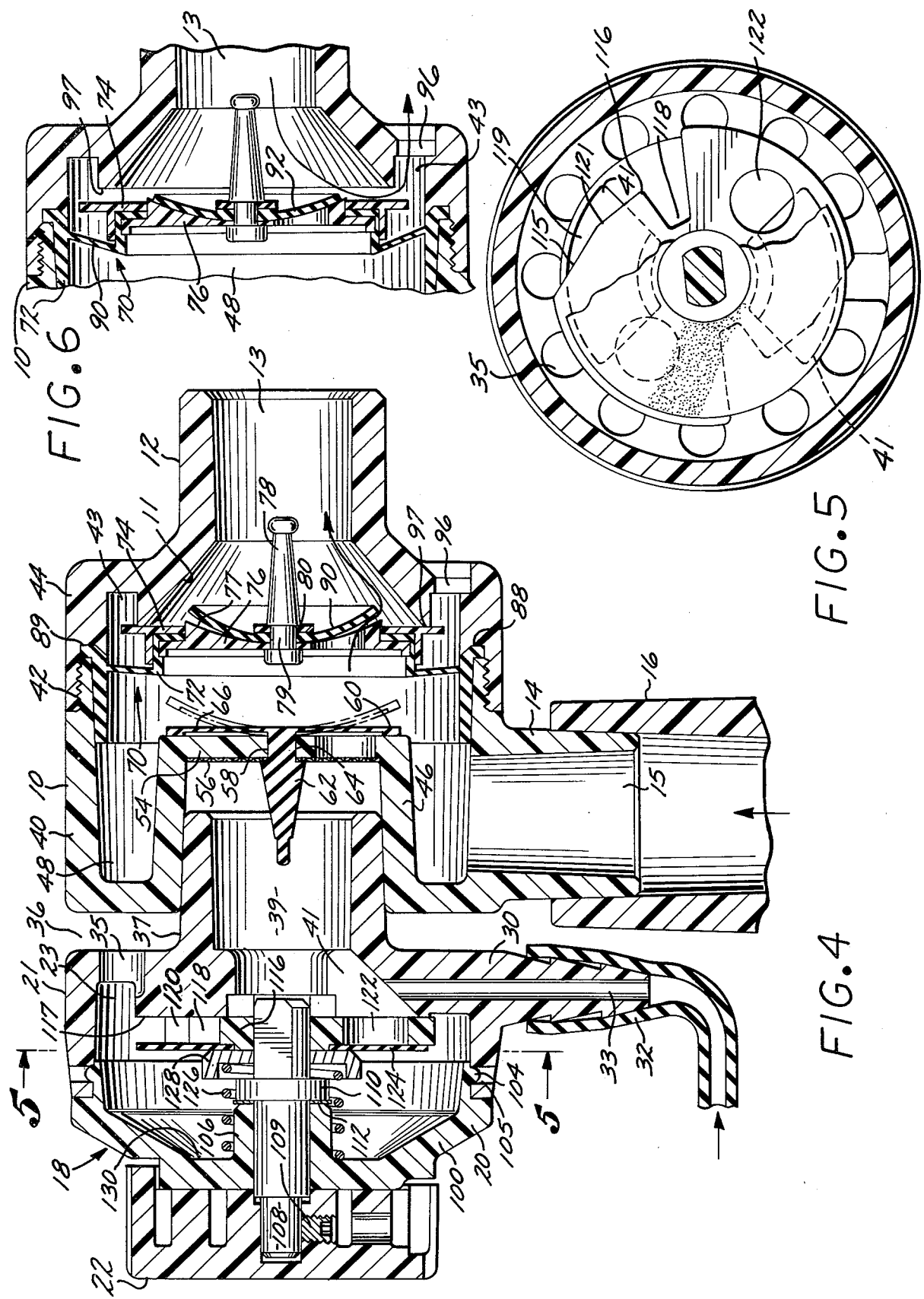

SQUEEZE BAG RESUSCITATOR WITH AIR-OXYGEN PROPORTIONATING CONTROL

BACKGROUND OF THE INVENTION

1. Field of the Invention

This invention relates to resuscitating devices and, in particular, to a squeeze bag resuscitator.

2. Brief Statement of the Prior Art

Various devices have been developed for forced resuscitation. These devices have included inhalation-exhalation valves such as described in U.S. Pat. Nos. 3,616,813 and 3,435,839. These valves permit the pressured discharge of an oxygen containing gas into the patients mouth and cyclic reversal to withdraw waste gases from the patient in a sequential manner.

The resuscitating devices have been provided with flexible squeeze bags of approximately one liter capacity and which are manually squeezed by the therapist in a rhythmatic or cyclic operation. Typical of these devices is that described in U.S. Pat. Nos. 3,473,529 and 3,202,446.

Another approach utilizes the pressure of the available oxygen supply for the operation of the resuscitator. These devices employ valves to apply the positive pressure of the oxygen supply to the resuscitator in a cyclic manner. Typical of demand valves are those described in my prior U.S. Pat. Nos. 3,795,257 and 3,285,261.

None of the devices which have been developed heretofore have provided a variably adjustable proportionating control whereby the oxygen content of the breathing gas mixture delivered by the resuscitator can be varied in preselected, precise portions. While the squeeze bag devices are generally desirable to provide the therapist with a "feel" or feed-back of the patient's lung response, these devices do not permit variable adjustment of the proportions of oxygen in the delivered mixture nor precisely control the composition of the delivered gas mixture.

BRIEF STATEMENT OF THE INVENTION

This invention comprises a resuscitating device of the squeeze bag configuration. The device comprises a resuscitator housing having a port communicating with the squeeze bag and another port communicating with a face mask and the like through an inhalation-exhalation valve which is operative to direct the breathing gas mixture to the face mask under positive pressure developed in the housing chamber by the squeeze bag. An inlet port to the housing bears a check valve operative to close the inlet port under positive pressure within the chamber and the housing has means to detachably secure the proportionating valve means of the invention to discharge into the housing through the inlet port.

The proportionating valve means of the invention has means to receive separate flows of oxygen and air and variable proportionating means to provide any of a plurality of preselected proportions of air and oxygen and discharge means to discharge the resultant mixture of air and oxygen to the resuscitator housing. The discharge means of the proportionating valve can be removably seated in attachment means of the resuscitator housing thereby providing a squeeze bag resuscitator with variable proportionating means to prepare and deliver a breathable gas mixture of preselected, variable proportions of oxygen.

BRIEF DESCRIPTION OF THE DRAWINGS

The preferred embodiment of the invention will be described with reference to the illustrations of which:

FIG. 1 is a perspective view of the invention;

FIG. 2 is an exploded assembly drawing of the components of the invention;

FIG. 3 illustrates the interchangability of the proportionating valve of this invention and oxygen demand valves of prior designs;

FIG. 4 is an elevational sectional view of the resuscitator with the proportionating valve of the invention;

FIG. 5 is a partial sectional view of the resuscitator valve during exhalation operation; and FIG. 6 is a view of the variable proportionating means of the invention.

DESCRIPTION OF THE PREFERRED EMBODIMENTS

Referring now to FIG. 1, the resuscitating device of the invention is illustrated as including a resuscitator housing 10 having a projecting neck 12 from one face thereof for discharge of a breathing gas mixture to a breathing mask, hose and the like. The housing 10 also has a radially projecting neck 14 to which is attached squeeze bag 16. The proportionating valve 18 is removably fitted to the face of the resuscitator housing 10 opposite of neck 12. This valve includes a regulator valve housing 20 and a proportional selector knob 22 having a pointer 24 to register with a plurality of indicia 26 indicative of the oxygen flow rate in a convenient units, typically in liters per minute. The regulator valve has means to receive a supply of oxygen including hose fitting 30 to which is attached a hose 32 leading from a source of pressurized oxygen. Although not apparent from the FIG. 1 illustration, the regulator valve 18 also has means to receive a flow of ambient air. This flow is received through apertures in the inboard face 34 of the valve housing 20; the flow passing through the annular slot 36 between the regulator valve 18 and the resuscitator housing 10.

Referring now to FIG. 2, the components of the resuscitating device of the invention are shown in exploded assembly. As there illustrated, the resuscitator housing is formed of two cylindrical members; base member 40 which bears radial neck 14 and which has an externally threaded open end 42 for the removable attachment of the cover member 44 which completes the housing. The base member 40 has a coaxial cylindrical well 46 projecting inwardly from face 48 and the internal walls of well 46 and the cylindrical base member 40 form an annular cavity 49 therebetween.

The inboard face 50 of well 46 has a plurality of open sectors 52 separated by radial ribs 54. A screen 56 is carried with well 46, overlying ribs 54. A center aperture 58 is provided in face 50.

A flexible disc 60 having an integral shank 62 is provided as a valve closure 66 member to cooperate with the open face 50 of well 46 to provide a check valve structure. Shank 62 has an annular groove 64 adjacent the disc 60 of this valve closure member. Shank 62 is resiliently received in aperture 58 which seats in annular groove 64 to secure the closure member 60.

The remainder of the resuscitating housing and internal parts is essentially the same as that described in my aforementioned prior patent. This structure includes an inhalation-exhalation valve means 70 having a valve closure member 72 formed of a flexible material such as rubber and the like which is sandwiched between a first, large diameter radial flange member 74 and a second, lesser diameter radial flange member 76. The assembly is secured by shaft 78 which has an annular groove that receives central apertures, such as 80, of flange members 74 and 76 in a snap fit.

Each of the flange members 74 and 76 have a central opening spanned by radial ribs such as 82 and 84 of flange members 74 and 76, respectively. The valve closure member 72 has an annular skirt 86 with an annular flange 88 and an annular face 90 which is received between the first and second radial flange members 74 and 76. The annular face 90 is integral with the central disc 92 which depends from integral radial ribs 94, the disc 92 serving as a flexible valve closure member to seal the central openings through radial flange members 74 and 76.

The cover member 44 of the resuscitator housing 10 has a plurality of arcuate slots 96 in its outboard face 98 which supports the adapter neck 12. The neck 12 provides communication with breathing apparatus such as a face mask and the like.

The regulator valve of the invention includes a housing 20 formed of a cylindrical base member 21 which bears radially projecting hose adapter 30 which can have a plurality of annular grooves 31 for securing flexible hose 32 from the pressurized oxygen supply. The annular face 34 of base member 21 bears a plurality of through apertures 35 and supports a coaxial neck 37 having a through passageway 39. Neck 37 has an outside diameter permitting it to be yieldably received within well 46 on the face 48 of the resuscitator housing 10.

The valve housing is completed with the end member 100 which has an axial flange 102 having raised bead 104 which is yieldably received within an annular groove on the inside wall of base member 21. The end member 100 has a coaxial, inwardly projecting boss 106 having a central aperture which receives shaft 108. The outboard end of shaft 108 carries the selector knob 22 which is attached thereto by suitable means such as a set screw and the like. The inboard end of shaft 108 is secured in the assembly by shaft shoulder 110 with a annular spring washer 112 provided in the assembly to provide appropriate tension of the selector knob.

The inboard end of shaft 108 has flats 113 which are received in the central aperture 114 of valve member 116. Aperture 114 has cordal flats to index to the flats 113 of shaft 108. Valve member 116 has a pair of opposed, radial slots 118 which are contiguous with peripherally relieved segments 120 to provide a variable orifice closure member with the internal structure of base member 21 of the housing as described in greater detail with reference to FIGS. 4 and 5. The valve member 116 also has a pair of apertures 122.

The valve member 116 is overlayed with a circular disc 124 of a flexible sheet material such as rubber and the like. Resilient means in the form of helical coil spring 126 is captured between spring retainer ring 128 and the inboard annular face 130 of end member 100. Spring 126 resiliently biases the valve member 116 against the opposing and cooperating valve structure internal of base member 21 as described with reference to FIGS. 4 and 5.

A feature of the instant invention is that the regulator valve 18 of the invention is detachably secured in the assembly and can be removed entirely, thereby permitting the resuscitating device to receive ambient air through the open face 50 of well 46. Alternatively, the resuscitating housing 10 can receive a demand valve 132, shown in FIG. 3, which is of the structure described in my aforementioned prior patent. This demand valve has an adapter neck 134 which is received within the well 46 which has a slightly tapered sidewall. The demand valve 132 is triggered by the vacuum created when the squeeze bag 16 is refilling and admits oxygen from the oxygen supply conduit 138 directly into the annular chamber 48 of the resuscitator housing 10, filling squeeze bag 16 with oxygen.

Referring now to FIGS. 4 and 5, the structure of the regulator valve and resuscitating unit will be described in greater detail. As there illustrated, the resuscitator unit has a housing 10 formed of the base member 40 and cover member 44 joined by threaded engagement. The internal chamber 49 of the housing 10 is in open communication with squeeze bag 16 by the through passageway 15 of neck 14. The cover member 44 supports neck 12 having through passageway 13 which communicates with a tapered transition section 11.

The inboard face of cover member 44 has an annular groove 43 which is in open communication with the arcuate through slots 96 and which forms an annular valve seat 97. The inhalation-exhalation valve means 70 is secured in the assembly with its annular flange 88 captured between the mating edges of base member 40 and end member 44 in the threaded joint of these members. An annular groove 89 can be provided in the closure member 44 to receive the annular flange 88.

As previously mentioned, the inhalation-exhalation valve means 70 comprises an assembly of the first radial flange member 74 and second radial flange member 76. The outboard face 77 of the second radial flange member 76 is preferably slightly convex and serves as a seat for the flexible central disc 92 which is shown in a deflected position, typical of the inhalation operation of the device wherein a positive pressure internal of chamber 49 permits the flow of a respirating gas mixture in the direction of the arrowhead line. As previously mentioned, the assembly of the first and second radial flange members 74 and 76 and the flexible valve closure member 72 is secured by shaft 78 which has an annular groove 79 that is captured in the central apertures, such as 80, of the first and second flange members.

Referring now to FIG. 6, the inhalation-exhalation valve means 70 is shown in the position characteristic of the exhalation operation. In this operation, the assembly is deflected inwardly by the reduced pressure within the central cavity 48 of housing 10. The annular face 90 of the flexible closure means 70 deflects the entire assembly inwardly to lift the annular face of the first radial flange member 74 from the valve seat 97, permitting the flow of gas through passageway 13, into annular groove 43 to the atmosphere through arcuate slots 96 as shown by the solid, arrowhead line of the figure.

Referring now to FIG. 4, well 46 which projects inwardly into chamber 49 bears the check valve means to permit entrance of a respirating gas into chamber 49 when this chamber is at reduced internal pressures and to seal the chamber when the latter is at positive internal pressures. The check valve includes disc 60 which is shown in its sealed position in the solid lines and its deflected or open position in the broken, phantom lines. The disc 60 is retained in the assembly by shank 62 having annular groove 64 that is captured in aperture 58 at the center intersection of ribs 54 of well 46. The foraminous screen 56 is likewise secured in the assembly by the annular groove 64.

The proportionating valve 18 employed in the invention includes housing 20 formed of the base member 21 which has the adapter neck 37 which is received within the tapered well 46 and which has through passageway 39 that communicates with a pair of opposite, outwardly flared ports 41. These ports are shown in better view in FIG. 5. The base member 21 also has an interior annular groove 23 which is in open communication with the plurality of through apertures 35 that open to the slot 36 between the proportionating valve 18 and the resuscitator housing 10. The end member 100 of the proportionating valve housing is secured to the base member 21 with beads 104 captured within annular slots 105 through the wall of the base member 21. The selector knob 22 is secured to shaft 108 by set screw 109. The shaft extends through the central aperture of internal boss 106 which is integrally carried on the inside face of closure member 100 and is retained by shaft shoulder 110 with a spring washer 112 captured between the end of boss 106 and shaft shoulder 110 to provide a resilient tension on the selector knob.

As previously mentioned, the valve member 116 of the proportionating valve is carried on the inboard end of shaft 108 and is resiliently biased against face 117 of the base member 21 by the helical coil spring 126 which is captured between spring retainer 128 and interior face 130 of closure member 100.

The valve member 116 has a pair of apertures 122, a pair of radial slots 118 and peripherally relieved segment portions 120. These elements appear in better illustation in FIG. 5 where the relieved segment areas can be seen to be formed by intersection of flat cordal surfaces 115 and 121. The resultant structure provides a variable orifice area 119 by the registration of the relieved segment areas 120 and/or radial slots 118 with the port 41 that discharge into passageway 39. The resultant, variable orifice is in the flow path of air entering apertures 35 and passing into the interior chamber of the proportionating valve to exit into through passageway 39.

The base member 21 also carries the hose adapter 30 which receives a flexible hose 32 from a pressured source of oxygen. The oxygen is supplied through the through passageway 33 of the adapter into the ports 41 to pass in the through passageway 39 to the resuscitor housing 10.

The proportionating valve is also provided with pressure relief means to prevent the valve assembly from locking against the exhalation operation in the event of high oxygen supply pressure and/or to bypass the flow of oxygen during the inhalation operation of the device. The pressure regulating means includes through apertures 122 in the proportionating valve member 116 and the flexible disc 124 which overlies the apertures 122. During the inhalation period, when the squeeze bag is collapsed to create a positive pressure in cavity 48 of the resuscitor housing 10, the check valve of flexible disc 66 closes and any oxygen supplied from the oxygen source through passageway 33 is bypassed through apertures 122 and deflected disc 124 into the interior of the proportionating valve housing to exit therefrom through apertures 35.

The operation of the device is fairly apparent from the preceding description. In the operation, the therapist need only select the desired oxygen demand for the patient under treatment by turning the selector knob 22 to a value from 0 to 15 liters per minute to correspond with the rate of oxygen being supplied from the pressurized oxygen source. As commonly practiced with squeeze bag resuscitators, the squeeze bag 16 has the appropriate volume and resiliency to provide an adult resuscitation cycle rate of from 12 to about 16 cycles per minute. Therefore, with the selector knob 22 set at the 15 liter per minute position and the oxygen supplied at a rate of 15 liters per minute, the cycle rate would be approximately 15 cycles per minute and the oxygen concentration would be approximately 100 percent. Accordingly, when the selector knob 22 is set at a value less than 15 liters per minutes, e.g., at 10 liters per minute and the oxygen supplied at a rate of 10 liters per minute, the cycle rate would remain approximately 15 cycles per minute but the oxygen concentration would decrease to approximately 74 percent. The therapist knows that at the above 10 liter per minute setting gas delivery to the patient is at a rate of 10 liters per minute of oxygen and 5 liters per minute of air.

The device is placed in operatin by supplying oxygen to the proportionating valve through a suitable and conventional pressure regulator, selecting the desired oxygen proportion in the resuscitating gas mixture and squeezing the squeeze bag several times to purge its contents and fill it with the desired resuscitating gas mixture. The face mask, of conventional design, is placed over the patient's face and the squeeze bag 16 is collapsed to discharge the resuscitating gas mixture through the inhalation-exhalation valve 70 and passageway 13 of adapter neck 12. The positive pressure created in chamber 48 of the housing 10 by the forced collapse of squeeze bag 16 closes the check valve in the gas supply to the squeeze bag by deflecting flexible disc 60 firmly against its seat. The continued supply of oxygen through hose 32 is thereafter bypassed by lifting flexible disc 124 from valve member 116, permitting escape of the oxygen gas through apertures 122 into the interior of the proportionating valve 18 and through apertures 35 in the back wall thereof. The positive pressure within the squeeze bag 16 also lifts flexible disc 92 from its seat permitting discharge of the resuscitating gas mixture within the bag along the arrowhead lines of FIG. 4, for delivery to the face mask and the like of the device.

The release of the external pressure on the squeeze bag 16 and the natural resiliency of the bag will develop a subatmospheric pressure within chamber 48, inducing exhalation from the patient's lungs through the face mask and will close the flexible disc 92 against its valve seat. The reduced pressure within chamber 49 of the resuscitating housing 10, lifts flexible check valve closure disc 60 from its seat, permitting inflow of the resuscitating gas mixture.

The resuscitating gas mixture is formed in any preselected proportions, depending upon the area of the orifice 119 in the air inlet flow passageway. When the selector knob is turned to the 15 liters per minute of oxygen setting, orifice 119 is closed and substantially no air enters the resuscitator unit. At this setting, the resuscitating gas mixture is substantially that supplied through hose 32, typically pure oxygen. As the selector knob is turned counterclockwise in the view shown in FIG. 1, the variable orifice 119 increases in area, permitting an increasing quantity of air to be introduced into the squeeze bag and diluting the oxygen content of the resultant resuscitating gas mixture.

The resuscitating unit of the invention can be utilized with or without the proportionating valve mechanism. When the resuscitating unit is employed with no supplemental gas supply, it will, of course, deliver air as the resuscitating gas mixture. When the demand valve of my prior invention is connected to the resuscitating housing in the manner illustrated in FIG. 3, the patient can be supplied with pure oxygen. Alternatively, the proportionating valve of the invention shown in detail in FIGS. 4 and 5 can be employed to provide any preselected proportions of the resuscitating gas mixture.

The invention has been described with reference to the presently preferred and illustrated embodiment. It is not intended that the invention be unduly limited by this disclosure of the presently preferred embodiments. Instead, it is intended that the invention be defined by the means, and their obvious equivalents, set forth in the following claims.

What is claimed is:

1. A squeeze bag resuscitating device comprising an assembly of a resuscitating valve housing having a squeeze bag connected thereto and containing an inhalation-exhalation valve means with mask attachment means for connection of said valve housing to a breathing mask and the like and gas inlet means including check valve means within said housing to close said gas inlet means under positive pressure in said squeeze bag, proportionating valve means detachably secured to said resuscitating valve housing and having means to receive separate flows of oxygen and air thereto, proportionating means to blend said oxygen and air flows to a preselected proportional gas mixture and discharge means to discharge said gas mixture to said gas inlet means of said valve housing said gas inlet means defining a socket, said discharge means defining an extension complementally and removably fitted within said socket.

2. The resuscitating device of claim 1 which includes pressure regulating means in said proportionating valve means to vent oxygen during the inhalation operation.

3. The resuscitating device of claim 1 wherein said proportionating means is fixedly adjustable to permit selection of a plurality of gas mixtures.

4. The resuscitating device of claim 3 wherein said proportionating valve means includes variable orifice means receiving said flow of air with adjustment means permitting fixed adjustability in said variable orifice means.

5. The resuscitating device of claim 4 wherein said adjustment means permits closing said variable orifice to said air flow to discharge oxygen only, to said squeeze bag.

6. A breathing apparatus comprising:
  (a) a resuscitating valve housing having a central chamber with inhalation, exhalation, squeeze bag and gas inlet port means;
  (b) inhalation-exhalation valve means mounted in said housing to discharge breathing gas from said central chamber through said inhalation port means during inhalation operation and to vent exhaled gas to said exhalation port means during exhalation operation;
  (c) squeeze bag means;
  (d) means to connect said squeeze bag means in open communication with said central chamber through said squeeze bag port means;
  (e) check valve means to close said gas inlet port means under positive pressure in said central chamber;
  (f) proportionating valve means having a proportionating valve housing with an interior chamber and discharge port means and first and second gas inlet port means, means to supply oxygen and air, respectively to said first and second gas inlet port means and orifice means within said interior chamber between said discharge port means and said gas inlet ports to prepare a mixture of oxygen and air of preselected proportions;
  (g) means to detachably secure said proportionating valve housing to said resuscitating valve housing with said discharge port means of said proportionating valve housing in communication to said gas inlet port means of said resuscitating valve housing; and
  (h) said detachable means comprises said gas inlet port means defining a socket, said discharge port means defining an extension complementally and removably fitted within said socket.

7. The breathing apparatus of claim 6 including pressure regulating means, in said proportionating valve housing to vent oxygen during inhalation operation of said breathing apparatus.

8. The breathing apparatus of claim 6 wherein said orifice means comprises variable orifice means with adjustment means carried by said proportionating valve housing to permit fixed adjustability of said variable orifice means whereby the proportion of oxygen in said mixture can be preselected to any of a plurality of proportions.

9. The breathing apparatus of claim 8 including indicia calibrated in oxygen flow rate values and cooperative index means carried by said adjustment means to indicate the preselected oxygen flow rate.

10. The breathing apparatus of claim 6 wherein said variable orifice is defined by cooperative stationary and moveable plates, each having at least one open, through portion moveable into and out of registration upon movement of the moveable plate to define a through orifice of variable area.

11. The breathing apparatus of claim 10 wherein said moveable plate is rotatably mounted in said proportionating valve housing.

12. The breathing apparatus of claim 11 wherein said proportionating valve housing is formed by a base member and a cover member, with said base member bearing said stationary plate to enclose said interior chamber with the through portion of said stationary plate communicating between said interior chamber and the discharge port of said proportionating valve housing.

13. The breathing apparatus of claim 12 wherein said moveable plate is mounted on a shaft carried by said cover member with resilient means also carried by said cover member to bias said moveable plate against said stationary plate.

14. The breathing apparatus of claim 12 wherein said second gas inlet port means comprises apertures in said base member communicating to said interior chamber.

15. The breathing apparatus of claim 14 wherein said first gas inlet port means communicates directly with the discharge port means of said proportionating valve housing.

16. A squeeze bag resuscitating device comprising:
  (a) a valve housing having a central chamber;
  (b) a first neck on the external wall of said valve housing having a through passageway;

(c) a squeeze bag attached to said first neck with its interior communicating with said central chamber by said through passageway;
(d) a second neck projecting from an external wall of said housing, for removable attachment of a face mask, with a second through passageway therein communicating with said central chamber;
(e) gas inlet means including check valve means within said housing to close said gas inlet means under positive pressure in said squeeze bag;
(f) inhalation-exhalation valve means operatively supported within said housing between said central chamber and said second through passageway; and
(g) receptacle means comprising a cylindrical well within a wall of said resuscitating valve housing having tapered sidewalls to removably receive a tapered neck of a gas supply valve means in open communication to said gas inlet means whereby a preselected unit of oxygen proportionating and oxygen demand valves can be interchangeably attached to said device.

17. The device of claim 16 wherein said second through passageway communicates exteriorly of said housing through exhalation port means and said inhalation-exhalation valve means.

* * * * *